United States Patent [19]

Wong

[11] Patent Number: 4,624,639

[45] Date of Patent: Nov. 25, 1986

[54] ADJUSTABLE OCCLUSAL PLANE TABLE AND METHOD OF USE FOR ORTHOGNATHIC SET-UPS

[76] Inventor: Brian W. Wong, 1672 Toyon Ct., San Mateo, Calif. 94403

[21] Appl. No.: 729,276

[22] Filed: May 1, 1985

[51] Int. Cl.⁴ .............................................. A61C 11/00
[52] U.S. Cl. ....................................... 433/56; 433/55; 433/63; 433/72
[58] Field of Search ............... 433/55, 56, 72, 73, 433/54, 57, 58, 59, 60, 61, 62, 63, 64, 65, 66, 67

[56] References Cited

U.S. PATENT DOCUMENTS

| | | | |
|---|---|---|---|
| 1,498,559 | 6/1924 | Lightcap | 433/56 |
| 1,598,535 | 8/1926 | Lentz | 433/61 |
| 2,748,481 | 6/1956 | Glueck | 433/55 |
| 4,171,570 | 10/1979 | Seldin | 433/73 |
| 4,391,589 | 7/1983 | Monfredo et al. | 433/63 |
| 4,449,929 | 5/1984 | Reese | 433/56 |
| 4,500,289 | 2/1985 | Garganese et al. | 433/54 |
| 4,504,226 | 3/1985 | Gordon | 433/63 |

FOREIGN PATENT DOCUMENTS 507874 12/1954 Canada .................................... 433/55

Primary Examiner—John J. Wilson
Attorney, Agent, or Firm—Fitch, Even, Tabin & Flannery

[57] ABSTRACT

An adjustable occlusal plane table for use with an articulator having a dental arch model mounted thereon includes a planar surface that is three dimensionally adjustable so as to be positioned along the plane of occlusion defined by the arch model. The occlusal plane table includes grid lines on the planar surface for recording the initial position of the arch model on the surface and for recording the change in position of the arch model with respect to the original plane of occlusion thereof. An intrusion ruler having equal steps formed along one edge is used to measure vertical displacement of said arch model from said occlusal plane surface.

9 Claims, 5 Drawing Figures

ADJUSTABLE OCCLUSAL PLANE TABLE AND METHOD OF USE FOR ORTHOGNATHIC SET-UPS

BACKGROUND OF THE INVENTION

This invention relates to orthognathic set-ups and more particularly to an apparatus and method for providing a plane of reference with respect to an arch model mounted in dental surgical instruments, such as an articulator.

Orthognathic dental surgery has achieved remarkable success with may patients. In this type of surgery, the position of one or both of the jaws of a patient are surgically altered. Although sometimes quite complicated and painful for a patient undergoing this surgery, the results achieved have been enormously beneficial both in its functional and in its aesthetic effects. Patients who formerly had gross malocclusions which distorted their appearance and made even the simple act of chewing food a chore have achieved a normal appearance and normal chewing process through dental surgery.

A number of techniques have been used in dental surgery to determine the extent to which the maxillary (upper jaw) and/or the mandible (lower jaw) need to be surgically adjusted in order to correct an existing malocclusion. The most accurate method currently known in the art involves the following technique. First, maxillary and mandibular arch models (dental casts) of the patient are made. Vertical and horizontal lines are then drawn on each model in a predetermined fashion so as to serve as reference points. After the arch models are mounted on an articulator so as to simulate and duplicate as accurately as possible the patient's malocclusion, position adjustments are made by cutting out wedges of material in an arch model (or models) and then seeing how the modified position improves occlusion and aesthetic appearance. The remaining arch model lines provide a rough indication of the extent of position modification performed.

It is a tedious and time consuming job to mark the arch models. Additionally, the lines are drawn by hand and are therefore inherently inaccurate. This becomes of critical importance when the dental surgeon attempts to reproduce the adjustments in the patient's mouth during surgery. Furthermore, when position adjustments are made, they almost always have an effect on more than just one plane. For instance, if a wedge or cut is made to shorten the jaw along the x axis, i.e., to adjust the jaw in the x direction, it will almost invariably affect the plane of occlusion along the y & z axes as well. It has been found to be very difficult to judge these effects using the above-described technique.

Consequently, there is a need to provide methods and devices which will enable more accurate determination of the position modification created in an arch model so as to enable its accurate implementation in a patient's mouth during surgery and to provide this function in a simple and easy to use way.

SUMMARY OF THE INVENTION

The method and apparatus of the present invention takes an entirely different approach to measuring changes made to the position of an arch model mounted in an articulator than as described above. A reference plane table adjustable in all three dimensions, i.e., along the x, y, and z axis, is positioned with respect to a selected arch model so as to simulate the patient's existing intraoral plane of occlusion. The plane table includes means for recording the starting position of the arch model on said planar surface and for recording the later position adjustments made to the arch model with respect to this starting position. The end result of this technique is a set of measurements in three dimensions that reflect the modifications made to the position of the arch model to create the aesthetic and functional improvement desired. These measurements are then used during surgery to enable much more accurate implementation of the predetermined arch model position modifications to the patient's jaw.

If a mistake is made in adjusting the arch model, the present invention also allows the dental surgeon to return the arch model to its starting position. Additionally, each recorded adjustment can be duplicated at a later time. An additional advantage is that the arbitrary reference plane table can be fitted to any articulator and the model transferred and worked on at another physical location without destroying all of the labor preceding such physical location switching.

It is therefore an object of the present invention to provide an apparatus and method of providing a reference plane for an arch model mounted in an articulator.

A more particular object of the present invention is to provide a referencing apparatus in an articulator which is capable of recording the starting position of the arch models and the position adjustments made thereto.

A further object of this invention is to provide a referencing apparatus for use with an articulator, which apparatus includes an adjustable planar surface defining an occlusal plane table which serves as a means for referencing the starting points and adjustment points of the model in the articulator.

Yet another object of the present invention is to provide an occlusal plane table that can be refitted to another articulator without losing the starting position of the arch model or the adjustments made thereto.

A still further object of the present invention is to provide a referencing apparatus in an articulator which measures adjustments in arch model position in the x, y, and z planes.

Generally, the apparatus of the invention comprises an adjustable occlusal plane table for use with an articultor, where the articulator has means for releasably holding a dental arch model thereto. The adjustable occlusal plane table has a planar surface and is adjustable so that this surface can be positioned so as to correspond to a patient's plane of occlusion as defined by the arch model. Means are also provided for referencing the initial position of the model along the planar surface of the plane table and means for measuring and recording the change in position of the model with respect to the original plane of occlusion.

Additional objects and advantages of the invention are made apparent in the following detailed description having reference to the accompanying drawings.

DETAILED DESCRIPTION OF THE PREFERRED EMBODIMENT

Articulators as well as other orthognathic instruments are used in dental surgery to simulate the patient's intraoral condition. As described above, a primary problem with present techniques and instruments is the inability to be able to accurately reference arch model position adjustments to the original starting point. This is especially difficult when an adjustment in one axis created an unintended displacement of the teeth in a different axis or direction.

The present invention enables the dental surgeon to reference and record the actual effect of any position adjustments in all three dimensions. The invention includes an occlusal plane table which is adjustable in three dimensions to the original occlusal plane of a patient.

Figure 1:
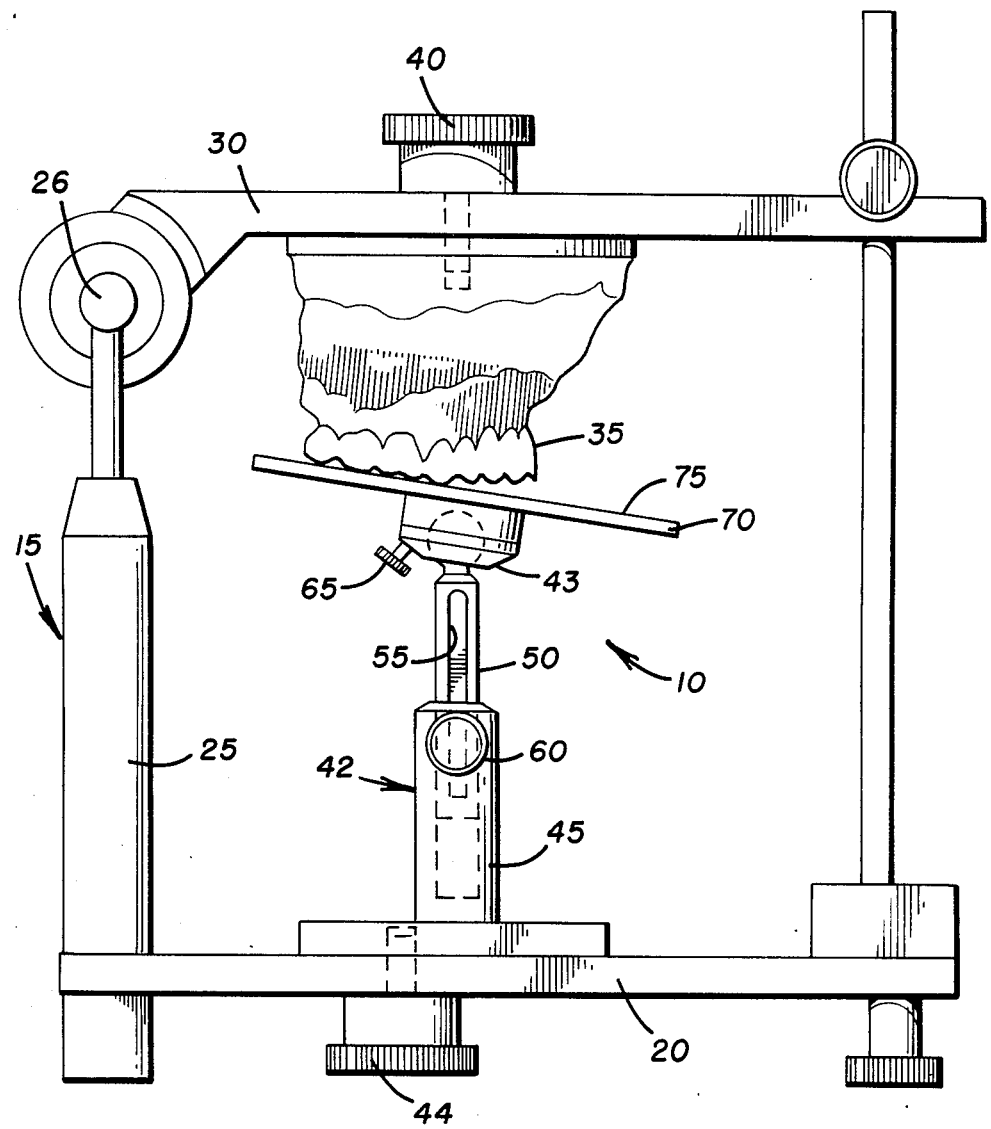
FIG. 1 is a side elevational view of an adjustable surgical articultor with an adjustable occlusal plane table in accordance with this invention.
Figure 4:
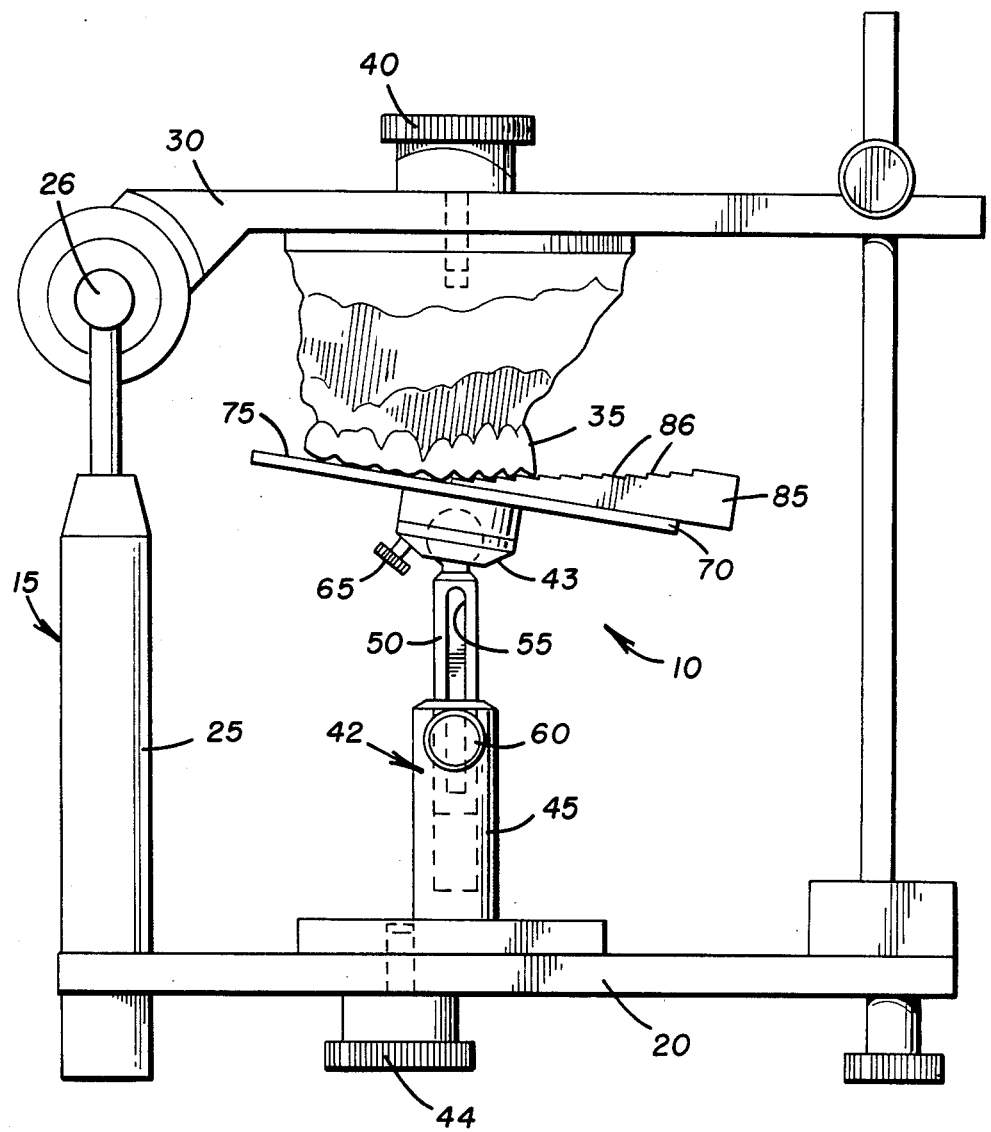
FIG. 4 is a side elevational view of the articulator of FIG. 1 illustrating use of the intrusion ruler of FIG. 3.

The initial step in using the apparatus according to the present invention is to transfer the patient's plane of occlusion to an articulator, i.e. to simulate a patient's malocclusion using maxillary and mandibular arch models mounted in an articulator. Conventional dental procedure is to start with adjustment of the upper jaw or maxillary arch model. Thus FIG. 1 and FIG. 4 show the present invention used with respect to this arch model. Referring now specifically to FIG. 1, shown at 10 is an occlusal plane table apparatus according to the present invention. The apparatus 10 is mounted in an articulator 15 and preferably takes the place of the mandibular arch model once malocclusion has been simulated by the articulator. The articulator 15 is preferably a commercially available articulator called a SAM articulator. The articulator includes a base 20 having upwardly extending support structure 25. A horizontal arm 30 from which the maxillary arch model 35 is suspended is hinged at hinge axis 26 to support 25. The maxillary arch model 35 is suspended by use of a screw 40 which is inserted into the model 35 as shown.

Apparatus 10 is mounted in place of a mandibular arch model in the SAM articulator and includes a shaft assembly 42. The bottom of shaft assembly 42 is mounted to the base 20 by means of a screw 44. Shaft assembly 42 also includes an adjustable sleeve 45. Reciprocally mounted within sleeve 45 and upwardly directed therefrom is a telescoping shaft or tube 50 having a slot 55 formed therein. As shown, shaft 50 is adjustable within sleeve 45 and fixable by means of adjustment screw 60. After the height of the shaft 50 is selected, the screw 60 is tightened to fix the height of shaft 50 at this point. Extending from shaft 50 is a specially designed ball and socket pivot joint 43 which is also adjustable and fixable in a conventional manner by means of an adjustment screw 65. Note that for ease of adjustment, both adjustment screw 60 and adjustment screw 65 can be elongated to provide easier access thereto.

An adjustable occlusal plane table 70 is shown connected to pivot joint 43. As will be appreciated, the occlusal plane table can be moved in any of the x, y, z axes or a combination thereof by means of movement of pivot joint 43 and shaft 50.

Figure 5:
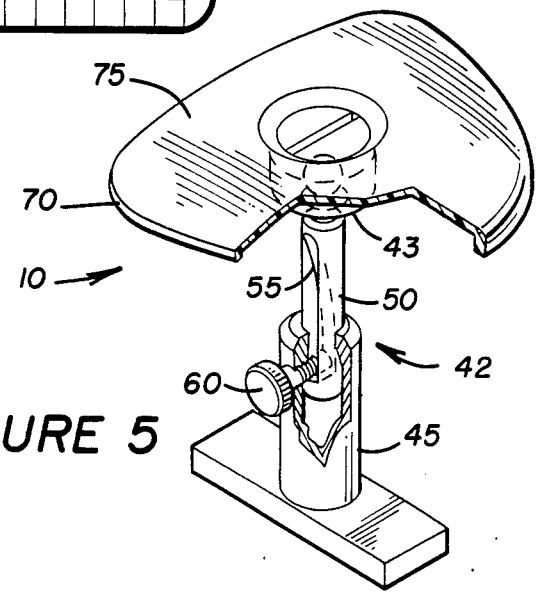
FIG. 5 is a perspective view of the occlusal plane table according to the present invention.

As best seen in the perspective view of the apparatus 10 shown in FIG. 5, the slot 55 formed in shaft 50 is tapered. This taper allows the occlusal plane table 70 to be finely adjusted in the vertical dimension by simply gradually loosening of adjustment screw 60.

The adjustable occlusal plane table 70 includes a planar or flat upper surface 75. The plane table and, more particularly the surface 75 is moved into contact or otherwise positioned as close as possible with three selected widely spaced apart cusp-tips on the maxillary arch model 35. The three cusp-tips are used to fix the plane table 70 with respect to the occlusal plane defined by maxillary arch 35. Contact is made by moving the adjustable shaft 50 upward and allowing the pivot joint 43 to be loose at the point of contact with model 35. Screws 60 and 65 are then tightened to fix the occlusal plane table 70 with respect to maxillary arch 35.

Figure 2:
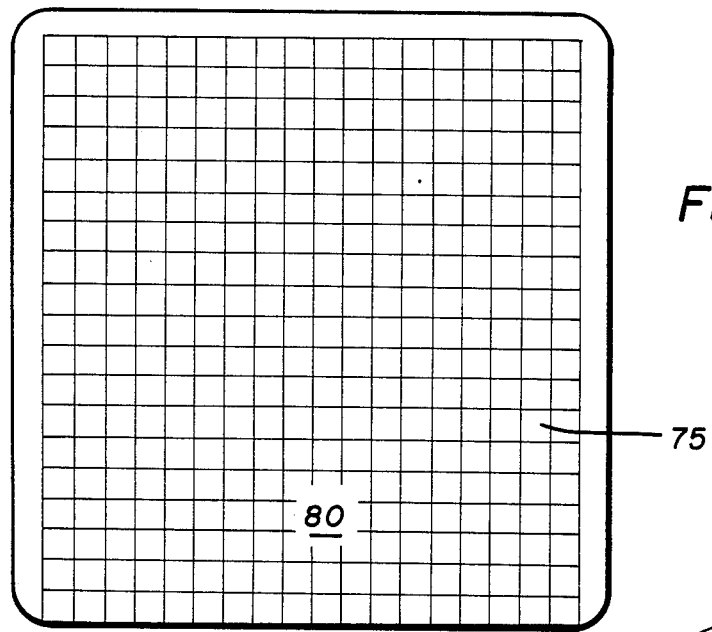
FIG. 2 is an enlarged elevated top view of the occlusal plane table of FIG. 1 having means for recording the starting position of the model and the adjustments made thereto.

FIG. 2 shows the top view of surface 75. Included on surface 75 is a sheet of graph paper 80. The graph paper grid lines (not illustrated to scale) are spaced preferably so as to enable the recording of position changes in increments of 1 mm or more. Graph paper 80 serves as a means for recording the starting point and subsequent adjustments made to the position of arch model 35. Other means for marking these position coordinates on a surface are also deemed to be a part of the present invention. After each position adjustment has been made to the maxillary arch model, the position of the cusp-tips on the table 70 are recorded.

Figure 3:
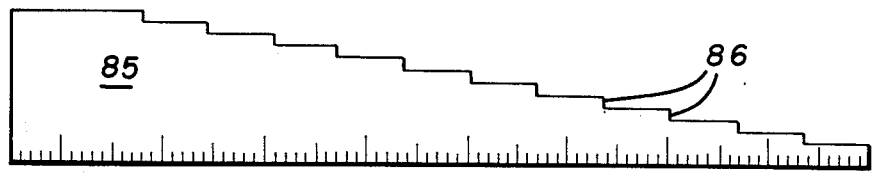
FIG. 3 is a side elevational view of an intrusion ruler used in conjunction with the occlusal plane table to measure the distance of the model from the table.

Since the arch model is adjustable along the x, y, and z axes, the user must be able to measure and record such movements. FIG. 3 illustrates an intrusion ruler 85, which preferably includes steps 86 having 1 mm increments. A standard horizontal millimeter scale may also be provided on intrusion ruler 85 for ease of measuring positional changes in the arch model 35 according to the present invention. Intrusion ruler 85 is used to determine the distance along the z axes of the cusp-tips from the surface 75 of table 70. Thus, as the arch model 35 position is adjusted by the dental surgeon, the model 35 may be shifted in the z direction off of the table 70 as illustrated in FIG. 4. The intrusion ruler 85 is used as shown to accurately measure the extent of this movement. If movement of the model 35 requires adjustment below the original plane of occlusion, screw 60 is loosened to allow the table 70 to drop along the z axis to accommodate this adjustment.

The graph paper 80 is preferably a removable self-adhesive millimeter graph paper which can be placed on another articulator or on the patient's chart. This enables arch model 35 to be later positioned on another articulator in exactly the same location without having to start with the original arch model 35 position. Thus, the use of the table 70 and the graph paper 80 recording means enables the dental surgeon to reproduce the arch model position adjustments on any articulator.

The maxillary arch model could, of course, be replaced by the apparatus 10 in order to do the same operations as described above to the mandible arch model. This is not typical practice for the reasons explained above.

Although it is believed clearly set forth above, the method of the invention will now be described. A method of making orthognathic adjustments to a patient's arch model in accordance with the present invention comprises the steps of making a dental arch model, mounting the arch model into an articulator so as to simulate the patient's plane of occlusion, fixing the occlusal plane, the starting point, by using three widely spaced apart cusp-tips and adjusting the occlusal plane table 70 described above to contact these cusp tips. The desired orthognathic position adjustments are then made to the arch model and these adjustments are recorded on graph paper 80 fixed on the surface 75 of the occlusal plane table 70.

Numerous variations both in connection with the occlusal plane table, the pivot joint, the recording means and the method as disclosed above are believed apparent. For example, other types of table, such as a table that is not planar but incorporates a Curve of Wilson, or different graph paper, or different articulators, may be used. Accordingly, the scope of the present invention is defined only by the following appended claims.

What is claimed is:

1. In an articulator having a dental arch model mounted thereon, a referencing apparatus comprising:
   a table having a generally planar surface;
   means for supporting said table on said articulator opposite to said arch model, including three dimensional adjustment means for positioning said planar surface at a selected plane with respect to said arch model; and
   means for recording the position of said arch model with respect to said planar surface and for measuring any changes in said arch model position with respect to said planar surface said means including graph paper positioned on said planar surface having grid lines of predetermined spacing along the x and y axes thereof corresponding to the x-y plane of said planar surface and an intrusion ruler having a plurality of steps of increasing height along the length of said ruler, each said step being a predetermined height.

2. The referencing apparatus of claim 1 wherein said means for positioning said planar surface at a selected plane with respect to said arch model comprises means for positioning said planar surface at the occlusal plane defined by said arch model.

3. The referencing apparatus of claim 1, wherein said intrusion ruler steps are each one millimeter in height.

4. In an articulator having a base, an upwardly extending support structure, and a horizontal arm hingedly mounted to said support structure and further including means for suspending a maxillary arch model from said horizontal arm, an improved adjustable occlusion plane table comprising:
   means for detachably mounting said occlusal plane table to the base of said articulator, said means including
   an upwardly extending sleeve attached to said base,
   a tube reciprocally mounted in said sleeve, said sleeve including means for fixably adjusting the height of said tube extending from said sleeve,
   a pivot joint mounted on the end of said tube opposite said sleeve, and
   means for mounting said occlusal plane table to said pivot joint, said occlusal plane table defining a planar surface on the opposite side of said plane table from said pivot joint, said pivot joint and said adjusting means enabling said surface of said occlusal plane table to be three dimensionally positionable with respect to the arch model; and
   means for recording the position of said arch model with respect to said planar surface and for measuring any changes in said arch model position with respect to said planar surface, said means including graph paper positioned on said planar surface having grid lines of predetermined spacing along the x and y axes thereof corresponding to the x-y plane of said planar surface and including an intrusion ruler having a plurality of steps of increasing height along the length of said ruler, each said step being of a predetermined height.

5. The occlusal plane table of claim 4 wherein said means for fixably adjusting the height of said tube comprises an adjustment screw threadably mounted in said sleeve and positioned to contact a vertically extending tapered slot defined in said tube.

6. In an articulator having a maxillary and mandibular arch model mounted therein so as to simulate the patient's existing intraoral plane of occlusion, a method for recording positional changes in either said maxillary or mandibular arch model needed to make orthognathic corrections to a patient's malocclusions comprising the steps of:
   (a) replacing either the maxillary or mandibular arch model with an occlusal plane table and aligning the surface of the plane table with the simulated occlusal plane of said patient's teeth as defined by the remaining said arch model;
   (b) marking the location of said remaining arch model on said occlusal plane table, including marking of vertical distances from selected teeth to said occlusal plane table;
   (c) measuring orthognathic changes in the position of said arch model in any of the x, y or z axes; and
   (d) marking the final location of said arch model on said occlusal table.

7. The method of claim 6 wherein said occlusal plane table defines an x,y plane and includes removable graph paper on its said surface having grid lines of redetermined spacing along the axes of said x,y plane, and wherein the step of marking of said arch model location on said occlusal plane table includes marking said location on said graph paper.

8. A method for measuring changes in the position of a maxillary or mandibular arch model with respect to the plane of occlusion defined by said arch model comprising the steps of:
   positioning the surface of an occlusal plane table at said plane of occlusion opposite said arch model;
   recording the position of said arch model on graph paper affixed to said surface of said occlusal plane table;
   measuring changes in position of said arch model along the x,y and z axes with respect to said occlusal plane table after orthognathic position adjustments have been made to said arch model including using an intrusion ruler having a plurality of steps formed thereon so as to measure incremental vertical displacements of said arch model off of the surface of said occlusal plane table; and
   recording said new position of said arch model on said graph paper.

9. The method of claim 8 wherein said plane of occlusion for positioning said occlusal plane table is defined by three widely spaced apart cusp-tips on said arch model.

* * * * *